United States Patent [19]

Lork

[11] Patent Number: 4,885,137
[45] Date of Patent: Dec. 5, 1989

[54] ZERO GRAVITY FLUIDIZED BED OPERATION

[75] Inventor: Wolfram Lork, Daisendorf, Fed. Rep. of Germany

[73] Assignee: Dornier System GmbH, Friedrichshafen, Fed. Rep. of Germany

[21] Appl. No.: 176,838

[22] Filed: Apr. 4, 1988

[30] Foreign Application Priority Data

Apr. 2, 1987 [DE] Fed. Rep. of Germany ....... 3711177

[51] Int. Cl.$^4$ .............................................. B01J 8/18
[52] U.S. Cl. .................... 422/140; 422/139; 422/141; 165/104.16; 261/83
[58] Field of Search ............ 165/104.16; 261/83; 55/91; 60/39.35; 422/140, 141, 139

[56] References Cited

U.S. PATENT DOCUMENTS 4,282,009  8/1981  Belke et al. .............................. 48/61
4,314,968  2/1982  Guigan .................................. 422/64
4,466,202  8/1984  Merten .

Primary Examiner—Barry S. Richman
Assistant Examiner—D. John Griffith, Jr.
Attorney, Agent, or Firm—Ralf H. Siegemund

[57] ABSTRACT

A wheel-like apparatus for the generation of whirling flow and a fluidized bed under zero gravity conditions having spokes which contain at least one reaction chamber for solid particles. Gas is fed into the chamber in radial inward direction for fluidizing action of the particles against any centrifugal force while liquid is sprayed into the chamber radially inwardly or outwardly. Gas plus vaporized liquid is extracted from the chamber in radial inner points and the gas is circulated back after separating the vapor from the gas.

4 Claims, 1 Drawing Sheet

ZERO GRAVITY FLUIDIZED BED OPERATION

BACKGROUND OF THE INVENTION

The present invention relates to the operation of whirl-flow, fluidized bed type reactors. More particularly the invention relates to a method and equipment for operating whirling flow layer, fluidized bed reactors in a zero gravity environment and involving particularly space technology, whereby the reactor to be moved into outer space may be a bioreactor or the like and its weight is to be drastically reduced while the process material is to be treated gently as compared with terrestrially operated, fluidized bed reactors.

Whirling flow and fluidized bed reactors are known to be comprised of a gaseous-solid system. Such systems are known generally from the literature in a variety of ways. They are used e.g. for thermal treatment of materials such as drying, cooling, in cracking processes, during coal burning, in the cement making industry as well as in biotechnology. In all these cases a gas stream or a flow of a watery solution is run through the process material and at a speed that is basically amenable or capable of loosening the process material so that it hovers or floats in a gaseous/liquid flow during operation while being passed through by the gas. This speed in which the material can be loosened is a minimal speed involving a continuously flowing phase so as to attain and maintain floating and hovering conditions.

Bioreactors are usually operated in the submerged mode i.e. the process material hovers and floats in a watery solution on the basis of its specific weight. That method is disadvantaged as compared with a fluidized bed system using a gas, for the following reason. First of all a higher substrate concentration is possible in a fluidized bed, and the gas injection and introduction into such a bed is simpler; any removal of residual process heat and the removal of volatile products themselves is easier than in a liquid system. Bioreactions are being discussed for various applications in space technology and it should also be mentioned that the manufacture of certain pharmaceutical products as well as biological life maintaining systems are of great interest. In a broad sense efficiency, generally and in specific terms such as weight and weight savings and space occupation, are all very important aspects.

Certain unsolved problems exist in the operation of whirling flow layer and fluidized bed bioreactors when operated on Earth. They are very sensitive to shear forces and abrasion, particularly with biological material such as certain cell structures. In case of a whirling flow, and mixing and blending this mutual abrasion is not to be neglected. This of course is added to the gravitational forces that act on these parts. The reactions require a gas flow which is sufficiently large so as to compensate the friction and the effect of gravity. The forces which are arising under these conditions are too large for sensitive cells. In the case of operating such a reactor in outer space there is no gravitational acceleration which is an advantage. That is also a disadvantage for stabilizing fluidized bed conditions.

DESCRIPTION OF THE INVENTION

It is an object of the present invention to provide a new and improved whirling flow layer, fluidized bed reactor in which missing forces of gravity are compensated in such a manner that physically damaging forces that act on the substance being fluidized are avoided.

In accordance with the preferred embodiment of the present invention it is suggested to replace the gravitational acceleration by a radial acceleration such that any solid material is kept floating in the gas or liquid flow even though the radial acceleration is smaller than regular Earth surface gravity. Preferably the reactors operated with moist gas i.e. enriched steam or air to which fluid is added preferably in a form of a watery solution. The fluid is injected through nozzles.

Specifically, the invention includes an apparatus in the form of wheel, wherein one or more spokes contain reactor chambers in which solid particles are treated in a fluidized bed that is generated through a radial inward gas flow. The gas is returned through other spokes for circulation. A liquid phase is introduced and vapor is separated from the gas in these other spokes.

The invention offers the advantage that the forces necessary for maintaining fluidized conditions are not fixed parameters such as the Earth's gravity but the acceleration in radial direction i.e. the centrifugal force can be adjusted to work exactly as desired and required under the circumstances which particularly makes sure that damaging forces of interaction will not occur on the biological substances. Also optimization is possible here with regard to moisture circulation. Any flow and reactor as per the invention reduces the mass and weight of a reactor for processing algae or bacteria. The reduction is down to about 1/20 of what has been used before. This is so since any liquid is added in forms of the moisture of the gas and not as pure liquid.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

Proceeding to the detailed description of the drawings, the figures show centrifuges 2 and chambers 2', having reactor chambers 4 in FIGS. 1 and 6 in FIG. 2 supplemented in each instance by auxiliary systems. The reactor chambers hold solid particles P to be treated in fluidized beds. Arrow R denotes centrifugal rotation. FIG. 2 shows a condensation chamber 8 and FIG. 1 shows a humidity controller 10. The reactor chambers face each other, so do the two humidity controllers 10 in FIG. 1 and the two condensation chambers in FIG. 2. This arrangement has the advantage that one can use these devices under terrestrial conditions, when gravity is present. Using gravity may involve e.g. the removal of condensation water.

The various pieces of equipment are arranged in spokes 12 which extend from a central chamber 14. The figures illustrate four such spokes, but this number is by way of example only, and of no restrictive significance. The spokes 12 carry a ring 16 which is hollow and subdivided in four segments. Segments 18 and 20 are provided for gas feeding and are separated from the remaining ring through separating walls or partitions 21.

Figure 1:
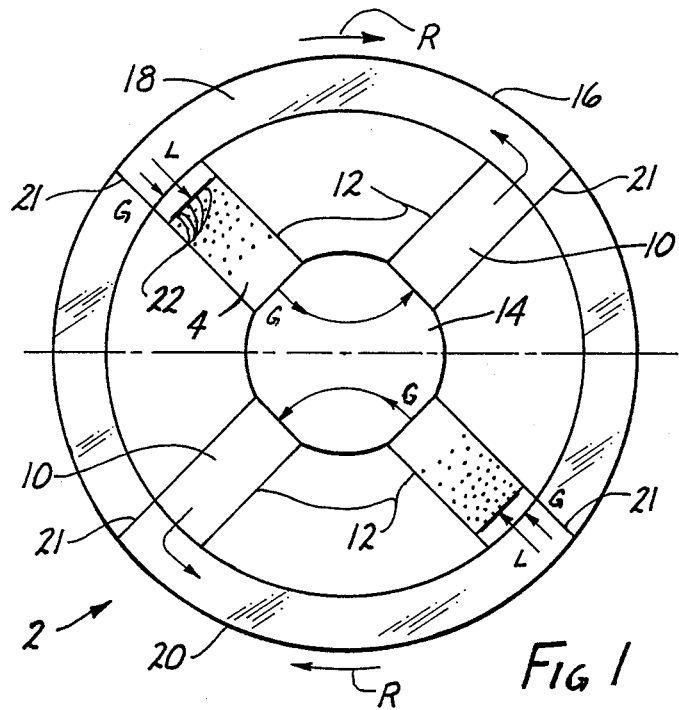
FIGS. 1 and 2 show two representative examples of the preferred embodiment of the present invention for practicing the best mode thereof; the figures differ in details concerning feeding of liquid but both of them show somewhat schematically a biological reactor centrifuge.
Figure 2:
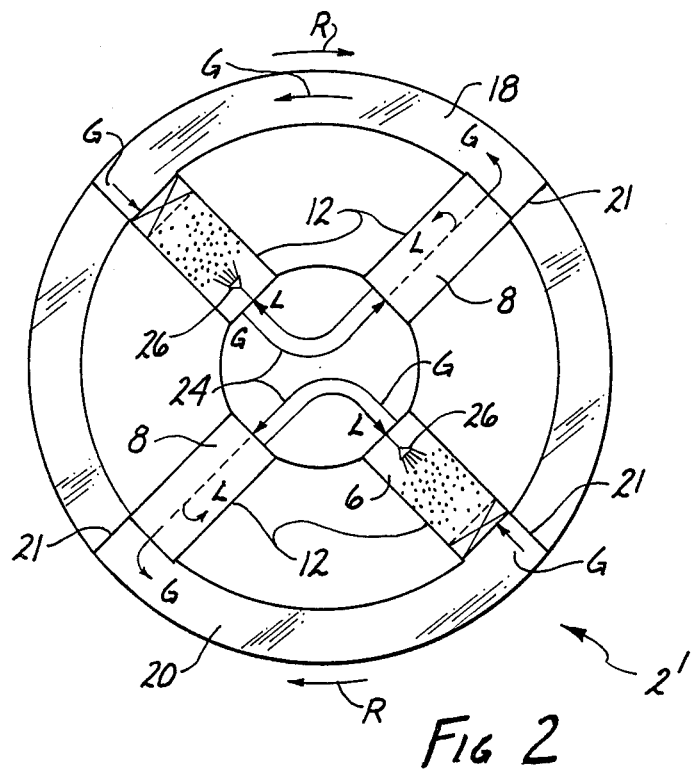

FIG. 1 shows in a first version, the feeding of liquid L and of gas G, the latter in a continuous process. In both instances, FIGS. 1 and 2, gas G flows radially inwardly through the particle layer P in the respective reactor chambers, 4 and 6. Hence, gas is pumped through the system against the centrifugal force in the respective chambers 4,6. FIG. 1 now shows specifically that the liquid phase L is fed through nozzles 22, i.e., it is sprayed in the chamber 4 also radially inwardly. FIG. 2 on the other hand shows nozzles 26 for feeding liquid in radial outward direction. Hence, the liquid is fed in one instance also against the centrifugal force (FIG. 1) but with the centrifugal force in the other instance, FIG. 2.

In order to maintain the articles P in a hovering, floating, and dynamically suspended condition and in the respective reactor chamber, the centrifugal force acts in both instances against the pressure and flow of the gas G. Thus, in FIG. 1 the gas is pumped to flow radially inwardly through the chamber 4. The liquid droplets are fed in the nozzle 22 and are carried along by the gas, but the centrifugal force acts in a radially outward direction and this keeps the droplets and particles floating to thereby establish the whirl flow, fluidized bed. The watery solution that is added will be completely converted into water vapor and the vapor is then carried along in the gas stream. In FIG. 1 this gas blend is fed through the humidity controller 10 wherein the humidity is reduced, and the dried gas flows through the segment 18; it is that gas which is pumped back into the reactor chamber 4.

FIG. 2 on the other hand shows that the liquid droplets to be carried by and in the gas flow actually flow in counterflow but are aided by the centrifugal force. The liquid evaporates and the steam flows with the gas through a duct 24 from which the gas steam blend enters the condensation chamber 8 wherein the blend is in fact subject to condensation. The liquid phase L is pumped back and into nozzles 26 while the gas G is passed through the segments 18 and 20 to be pumped into the respective radial outer end for chambers 6.

The invention is not limited to the embodiments described above but all changes and modifications thereof, not constituting departures from the spirit and scope of the invention, are intended to be included.

What is claimed is:

1. Apparatus for the generation of whirling flow and a fluidized bed under zero gravity conditions, comprising:
    a wheel-like configuration having a plurality of radially disposed spokes and means mounting said configuration for rotation about a central axis thereof;
    at least one reaction chamber for solid particles and being mounted in relation to and arranged in one of the spokes of the wheel-like configuration and thus being a part of a centrifuge, the chamber thus extending in a radial direction;
    means for feeding gas into each chamber in a radially inward direction for fluidizing the particles against any centrifugal force on accord of rotational movement of the wheel-like configuration;
    means for causing liquid droplets to be fed into each chamber;
    means for extracting gas plus vaporized liquid from each chamber at the radially innermost point of that chamber; and
    means for circulating the gas back to the means for feeding and including means for separating vapor from the gas prior to feeding it back to each reactor chamber through the means for feeding.

2. Apparatus as in claim 1, the separating means being arranged in another one of the spokes of the wheel-like configuration.

3. Apparatus for the generation of whirling flow and a fluidized bed under zero gravity conditions, comprising:
    a centrifuging wheel having a peripheral ring and a plurality of radial spokes extending from a central chamber to the peripheral ring and having means mounting said wheel for rotation about a central axis thereof;
    at least one reaction chamber for fluidizable solid particles and being mounted in one of the spokes for extending in a radial direction;
    means for feeding gas through each reactor chamber into the central chamber in a radially inward direction for fluidizing the particles in each reaction chamber against any centrifugal force, said gas then being fed to the central chamber; and
    means in at least another one of the spokes and connected for circulating the gas into the peripheral ring and for feeding it back to a respective reaction chamber.

4. Apparatus as in claim 3, there being means for spraying liquid into each reaction chamber, and means in said another one of the spokes for obtaining separate and condensed liquid to be fed back to the means for spraying.

* * * * *